United States Patent
Pan et al.

(10) Patent No.: US 10,395,928 B2
(45) Date of Patent: Aug. 27, 2019

(54) DEPOSITING A PASSIVATION LAYER ON A GRAPHENE SHEET

(71) Applicant: Nanomedical Diagnostics, Inc., San Diego, CA (US)

(72) Inventors: Deng Pan, San Diego, CA (US); Brett Goldsmith, San Diego, CA (US); Mitchell Lerner, San Diego, CA (US)

(73) Assignee: Nanomedical Diagnostics, Inc., San Diego, CA (US)

( * ) Notice: Subject to any disclaimer, the term of this patent is extended or adjusted under 35 U.S.C. 154(b) by 0 days.

(21) Appl. No.: 15/623,232

(22) Filed: Jun. 14, 2017

(65) Prior Publication Data
US 2017/0365474 A1 Dec. 21, 2017

Related U.S. Application Data

(60) Provisional application No. 62/350,634, filed on Jun. 15, 2016.

(51) Int. Cl.
*H01L 29/16* (2006.01)
*H01L 21/04* (2006.01)
*H01L 21/02* (2006.01)
*G01N 27/30* (2006.01)

(52) U.S. Cl.
CPC ....... *H01L 21/0405* (2013.01); *G01N 27/308* (2013.01); *H01L 21/02107* (2013.01); *H01L 21/02697* (2013.01); *H01L 29/1606* (2013.01)

(58) Field of Classification Search
CPC ........... H01L 21/02225; H01L 21/0226; H01L 21/0405; H01L 21/62; H01L 21/64; H01L 21/702; H01L 21/71; H01L 29/66007; H01L 29/68
See application file for complete search history.

(56) References Cited

U.S. PATENT DOCUMENTS

| | | | |
|---|---|---|---|
| 3,951,681 A | 4/1976 | Shoemaker | |
| 9,349,825 B2 | 5/2016 | Feng | |
| 2002/0115025 A1* | 8/2002 | Noda | G03F 7/42 430/329 |

(Continued)

OTHER PUBLICATIONS

MICROCHEMICALS, "Phtotoresist Removal", Nov. 7, 2013, p. 1, Retrieved from http:/lwww.microchemicals.com/technical_information/photoresist_removal.pdf on Nov. 22, 2017.

(Continued)

*Primary Examiner* — Cheung Lee
(74) *Attorney, Agent, or Firm* — Sheppard Mullin Richter & Hampton LLP

(57) ABSTRACT

Embodiments of the disclosed technology include depositing a passivation layer onto a surface of a wafer that may include a graphene layer. The passivation layer may protect and isolate the graphene layer from electrical and chemical conditions that may damage the graphene layer. As such, the passivation layer may further protect the graphene sensor from being damaged and impaired for its intended use. Additionally, the passivation layer may be patterned to expose select areas of the graphene layer below the passivation layer, thus creating graphene wells and exposing the graphene layer to the appropriate chemicals and solutions.

13 Claims, 3 Drawing Sheets

(56) References Cited

U.S. PATENT DOCUMENTS

| | | | | |
|---|---|---|---|---|
| 2012/0040522 A1* | 2/2012 | Cheng | ............... | H01L 21/82346 438/585 |
| 2012/0285527 A1* | 11/2012 | Goldblatt | .......... | H01L 31/02243 136/256 |
| 2013/0182373 A1 | 7/2013 | Yu | | |
| 2013/0217215 A1 | 8/2013 | Ward et al. | | |
| 2015/0038378 A1 | 2/2015 | Cheng et al. | | |
| 2015/0303059 A1 | 10/2015 | Friedman et al. | | |
| 2015/0364567 A1* | 12/2015 | Feng | ................ | H01L 29/42364 438/151 |
| 2015/0371848 A1* | 12/2015 | Zaretski | ............ | H01L 21/02527 438/496 |
| 2016/0033448 A1 | 2/2016 | Milgrew | | |

OTHER PUBLICATIONS

SAMATERIALS, "Advantages and Disadvantages of Graphene", Mar. 27, 2014, p. 1, Retrieved from https://samaterials.wordpress.com/2014/03/27/advantages-and-disadvantages-of-graphene/ on Nov. 22, 2017.

Song et al., "Corrosion Protection of Electrically Conductive Surfaces", Metals, Nov. 15, 2012, vol. 2, pp. 450-477.

Chen, "III. Wet and Dry Etching", Apr. 12, 2014, p. 1, Retrieved from http://www.mrsec.harvard.edu/education/ap298r2004/Erli%20chen%20Fabrication%20111%20-%20Etching.pdf on Nov. 22, 2017.

Patent Cooperation Treaty, International Search Report for PCT/US2017/037704, dated Sep. 6, 2017, pp. 1-2.

Desai, S. et al., Gold Mediated Exfoliation of Ultralarge Optoelectronically-Perfect Monolayers, Adv. Mater. 25, Mar. 23, 2016, pp. 4053-4058.

International Search Report and Written Opinion in International Application No. PCT/US2017/0337701, dated Sep. 6, 2017.

International Preliminary Report on Patentability in International Application No. PCT/US2017/037701, dated Dec. 18, 2018.

International Search Report and Written Opinion in International Application No. PCT/US2017/037764, dated Sep. 6, 2017.

International Preliminary Report on Patentability in International Application No. PCT/US2014/037764, dated Dec. 18, 2018.

International Search Report and Written Opinion in International Application No. PCT/US2017/033769, dated Sep. 6, 2017.

International Preliminary Report on Patentability in International Application No. PCT/US2014/037769, dated Dec. 18, 2018.

* cited by examiner

Figure 1A
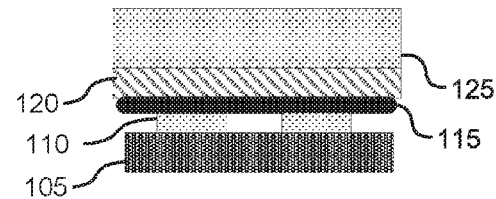
Figure 1B
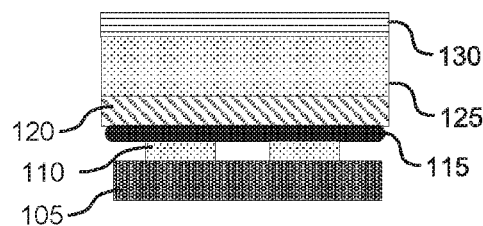
Figure 1C
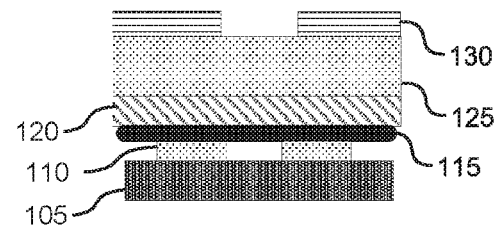
Figure 1D
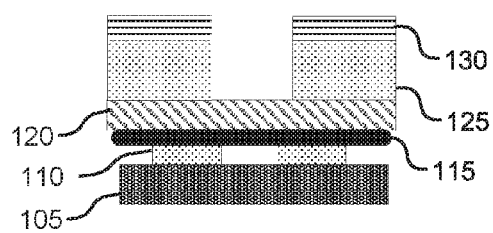
Figure 1E
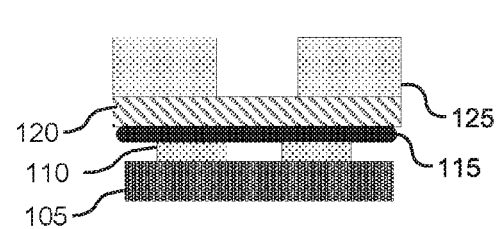
Figure 1F
Figure 1

DEPOSITING A PASSIVATION LAYER ON A GRAPHENE SHEET

CROSS-REFERENCE TO RELATED APPLICATIONS

This application claims the benefit of priority to U.S. Provisional Patent Application with Ser. No. 62/350,634 filed on Jun. 15, 2016, the contents of which are incorporated herein.

TECHNICAL FIELD

The disclosed technology relates generally to creating wells on a graphene sheet. More specifically, the disclosed technology relates to creating wells on a graphene sheet by depositing a passivation layer on top of the graphene sheet.

BACKGROUND

Graphene is composed of a single thin layer of carbon atoms that are bonded together in a repeating pattern of hexagons. Graphene has many extraordinary properties, which includes high mechanical strength, high electron mobility, and superior thermal conductivity. Because graphene is a great thermal and electrical conductor, graphene may be coupled to metal contacts or leads in biosensors and various diagnostic devices to provide accurate analytical measurements of chemical and biological samples.

However, preparing and incorporating graphene into biosensors or other diagnostic devices may be a difficult task, especially on a large manufacturing scale. This is because graphene may often be contaminated or damaged when creating wells on the graphene.

To prevent the contamination and shorting of the graphene sheets when handling and preparing them, current methods often directly treat the surface of the graphene sheet and its metal contacts with a photoresist layer or with a polymethylmethacrylate (hereinafter "PMMC") layer used as a resist film. However, this results in many undesirable secondary effects. For example, when applying the photoresist or PMMC layer directly onto the graphene, such direct contact contaminates the surface of the graphene sheets, and may even degrade the performance of the graphene when incorporated into biosensors or electronic devices. As such, there currently is a need to protect the graphene layer without contaminating or damaging the graphene layer when preparing and creating graphene wells.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 1 illustrates the different progressions of depositing a passivation layer onto a wafer for creating graphene wells according to one embodiment.

FIG. 1A illustrates a graphene sheet with a metal coating according to one embodiment.

FIG. 1B illustrates a passivation layer deposited onto a wafer with a graphene sheet according to one embodiment.

FIG. 1C illustrates a photoresist layer applied onto the surface of the passivation layer according to one embodiment.

FIG. 1D illustrates patterning the photoresist layer according to one embodiment.

FIG. 1E illustrates patterning the passivation layer in accordance to the exposed areas according to one embodiment.

FIG. 1F illustrates the removal of the photoresist layer according to one embodiment.

Figure 2:
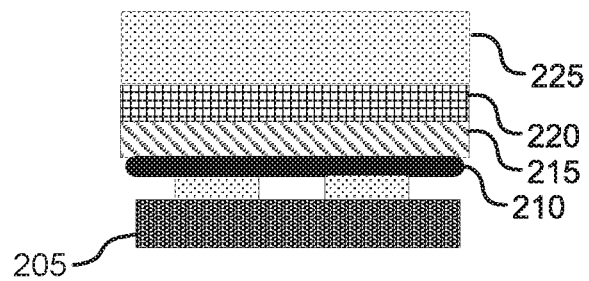
FIG. 2 illustrates a graphene sheet with a two different metal coatings on top according to one embodiment.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The following description is not to be taken in a limiting sense, but is made merely for the purpose of describing the general principles of the disclosed embodiments. The present embodiments address the problems described in the background while also addressing other additional problems as will be seen from the following detailed description. Numerous specific details are set forth to provide a full understanding of various aspects of the subject disclosure. It will be apparent, however, to one ordinarily skilled in the art that various aspects of the subject disclosure may be practiced without some of these specific details. In other instances, well-known structures and techniques have not been shown in detail to avoid unnecessarily obscuring the subject disclosure.

Embodiments of the disclosed technology include creating graphene wells by depositing a passivation layer on top of a wafer containing graphene. It should be noted that depositing layers onto the graphene sheet may include a wide range of techniques as appreciated by one of ordinary skill in the art, such as coating techniques, focused ion beam, filament evaporation, sputter deposition, and electrolysis by way of example only.

Some embodiments include depositing a uniform passivation layer to coat the metal leads that are electrically coupled to the graphene, such that the passivation layer may prevent the leaking of the electrical current through the metal leads. By way of example only, the passivation layer may be an dielectric layer, such as a silicon dioxide layer. However, the passivation layer need not be limited to silicon dioxide, and instead, may also include silicon nitride, silicon oxide, amorphous silicon, polysilicon and the like.

Additionally, further embodiments may also include exposing select areas of the graphene sensor surface by patterning areas of the passivation layer to expose the graphene sensor. To pattern the passivation layer, by way of example only, a photoresist layer may first be added to the top surface of the passivation layer so that the photoresist layer acts as a template for transferring the select pattern onto the passivation layer. More of this patterning process is explained in detail below.

With the passivation layer properly patterned, metal leads are now exposed and thus allowing for the chemical or biological sensing to occur. Furthermore, this then exposes the graphene layer immediately below the passivation layer. By transferring the pattern etched from the photoresist layer and the passivation layer, the graphene layer may be patterned accordingly to create the graphene wells.

FIG. 1 generally illustrates the different progressions of depositing a passivation layer onto a wafer for creating graphene wells according to one embodiment. As illustrated, FIG. 1A depicts a graphene sheet 115 with a first metal coating 120, such that the graphene sheet 115 may be placed on the surface of thin semi-conductor material, such as a wafer 105. The wafer 105 may serve as a substrate foundation upon which the proper electronic integrated circuits can be applied. Byway of example, the wafer 105 may be a silicon substrate or a silicon dioxide substrate. However, it should be noted that the wafer may also include material such as quartz, sapphire, or plastic. Additionally, the wafer 105 may be coated with platinum 110, whereby the platinum 110 acts as the bottom electrode.

Additionally, a first metal coating 120 may be deposited onto the surface of the graphene sheet 115, where the first metal coating 120 may act as a mask or barrier to protect the graphene from being contaminated or degraded. By way of example only, the first metal coating 120 may include gold. Because gold is an inert metal that has the characteristic property of being resistant to corrosion and oxidation, coating the graphene sheet with a gold layer on top may protect the graphene sheet 115. Additionally, due to gold's characteristically inert qualities, the gold coating on the surface of the graphene sheet 115 may further provide thermal protection and prevent oxidation, especially when the graphene is exposed to high temperature treatments during epoxy curing, oven baking, and burn testing. Furthermore, the gold coating may also protect the graphene from being potentially contaminated during wire bonding, encapsulation, wafer dicing, and cleaning as the graphene sheet 115 is being prepared for installation within a sensor or device by way of example only.

However, other inert metals may also be used to coat the graphene sheet, which may include, but are not limited to, metals that include ruthenium, rhodium, palladium, silver, osmium, iridium, platinum and the like.

To properly coat the graphene sheet 115 with the first metal coating 120, the surface of the graphene sheet 115 may initially be prepped by placing the wafer 105 with the graphene sheet 115 in an electron beam evaporation chamber. Electron beam evaporation is a physical vapor disposition technique whereby an intense electron beam is generated from a filament and steered via electric and magnetic fields to strike source material, such as gold pellets, and to vaporize it within a vacuum environment. As such, by using the electron beam evaporation technique, a thin first metal coating 120 may be slowly deposited onto the graphene sheet 115, where the first metal coating 120 may range in a thickness from 10 nanometers to 1 micrometer. By way of another example, the first metal coating 120 may be applied onto the graphene sheet 115 by dipping the graphene sheet 115 into a gold plating solution. Additionally, other methods of depositing a metal coating may also include utilizing a focused ion beam, filament evaporation, sputter deposition, electrolysis and the like.

Furthermore, a second metal layer (not shown in FIG. 1) may be deposited on top of the first metal coating 120. The second metal layer 220 is illustrated in FIG. 2. Here, the graphene sheet 210 may be deposited on top of a wafer, where a first metal coating 215 is deposited on top of the graphene sheet 210. Additionally, a second metal coating 220 may be deposited on top of the first metal coating 215. As discussed above, the first metal coating may a gold metal coating to protect graphene from being potentially contaminated during wire bonding, encapsulation, wafer dicing, and cleaning. However, other inert metals that do not negatively react with graphene may also be used to coat the graphene sheet, which may include, but are not limited to, ruthenium, rhodium, palladium, silver, osmium, iridium, platinum and the like.

Additionally, the second metal coating 220 may be deposited on top of the first metal coating 215. By way of example only, the second metal coating 220 may be a metal that oxidizes more easily than the first metal coating 215. The second metal coating 220 may also be referred to as an "adhesion layer" because the second metal coating 220 acts as an adhesive that sufficiently sticks onto the first metal coating 215 and also sticks onto the photoresist layer 225 directly above. As such, the second metal coating 220 may be a metal coating that has the characteristic properties that allow it to adhere onto the surfaces of the first metal coating 215 below and the passivation layer 225 directly above. By way of example only, the second metal coating 220 may include a metal layer that includes at least one of titanium, aluminum, chrome, nickel, and titanium nitride. More detailed information regarding the passivation layer 225 is provided below.

Referring back to FIG. 1, and FIG. 1B in particular, FIG. 1B illustrates a passivation layer 125 deposited onto a wafer 105 with a graphene sheet 115 according to one embodiment. By way of example, the passivation layer 125 may include a uniform layer of silicon dioxide that is coated onto the metal connector leads that are electronically coupled to the graphene sheet 115 on the wafer 105. In some embodiments, the graphene sheet 115 may be layered with a first metal coating 120, such that the passivation layer 125 is deposited on top of the first metal coating 120. However, it should be noted that the passivation layer 125 may be deposited on either the first metal coating 120 or the second metal coating (not shown here), as described above with reference to FIG. 2. Additionally, the passivation layer 125 need not be limited to a silicon dioxide layer, and instead, may also include silicon nitride, silicon oxide, amorphous silicon, polysilicon and the like.

To deposit the passivation layer 125 uniformly onto the wafer 105, a plasma enhanced chemical vapor deposition technique may be utilized. Plasma Enhanced Chemical Vapor Deposition (hereinafter "PECVD") may deposit a thin film, such as a thin silicon dioxide film on the wafer 105 at lower temperatures compared to other conventional deposition techniques. By way of example, the temperatures may range from 100° C. to 200° C. This allows for a gentler deposition technique to be utilized, which is also less likely to damage the graphene and the sensors or devices being fabricated. In the PECVD process, deposition is achieved by introducing reactant gases and then exciting the reactant gases into a plasma, which then induces a chemical reaction so that a thin layer of product is deposited onto the wafer 105. However, other deposition techniques may also be utilized to deposit a uniform passivation layer 125 onto the wafer 105, such as Inductively Coupled Plasma PECVD, sputtering, and electron beam evaporation by way of example only.

By utilizing any of the known deposition techniques known by those skilled in the art, the passivation layer 125 may range in a thickness from 100 nanometers to 1 micrometer. With the passivation layer 125 coated onto the wafer, the passivation layer 125 also provides a coated layer to the metal contact leads located on the surface of the wafer 105. As such, the passivation layer 125 may effectively reduce any reverse-current leakage, increase breakdown voltage, and even raise power dissipation rating. However, because the metal contact leads are formed on the wafer 105 and now currently coated with a passivation layer 125, the passivation layer 125 may be patterned to create wells in order to expose portions of the metal contact leads below to the chemical environment.

To prepare the patterning of the passivation layer 125, a photoresist layer 130 may be deposited on the wafer 105, as illustrated in FIG. 1C. The photoresist layer 130 may include photosensitive material that experiences a change in its physical properties when exposed to a radiation source. By selectively exposing the photoresist layer 130 with radiation, such exposed areas of the photoresist layer 130 may be etched away, thus exposing portions of the passivation layer 125 underneath the photoresist layer 130, as further illustrated in FIG. 1D. In other words, the etched pattern on the photoresist layer 130 acts as an etching template, such that the etched pattern is then appropriately transferred to the passivation layer 125 beneath the photoresist layer 130.

With a pattern properly etched onto the photoresist layer 130, the passivation layer 125 may now proceed to also be patterned according to the pattern etched onto the photoresist layer 130, as illustrated in FIG. 1E. As such, it is important that the photoresist layer 130 is unaffected by the radiation when etching the photoresist layer, so that only the photoresist layer is etched and patterned while the passivation layer 130 remains intact.

Thus, to etch away portions of the passivation layer 125, the passivation layer 125 itself may be etched via Reactive Ion Etching. Reactive Ion Etching is a method of dry etching that utilizes chemically reactive plasma to remove selected portions of the passivation layer 125. Thus, areas where the photoresist layer 130 still remains will continue to act as a barrier or protective layer since the photoresist layer 130 is inactive to Reactive Ion Etching. Additionally, because the graphene sheet 115 is also protected and covered with a gold metal coating 125, the graphene sheet 115 is also protected from the Reactive Ion Etching. In other words, the Reactive Ion Etching will only etch away the exposed passivation layer 125.

With the passivation layer 125 now patterned accordingly, metal leads or connections are now exposed, thus allowing the metal leads or connections to take the appropriate sensor measurements with the creation of these wells on the wafer 105 with the graphene sheet 115. Because the passivation layer 125 is also now patterned, the photoresist layer 130 may now be removed, as illustrated in FIG. 1F. For example, to remove the photoresist layer 130, the wafer 105 with the photoresist layer 130 may be rinsed with acetone for 2 to 10 minutes followed by isopropanol alcohol for another 1 to 5 minutes, thus effectively and completely removing the photoresist layer 130.

Figure 3:
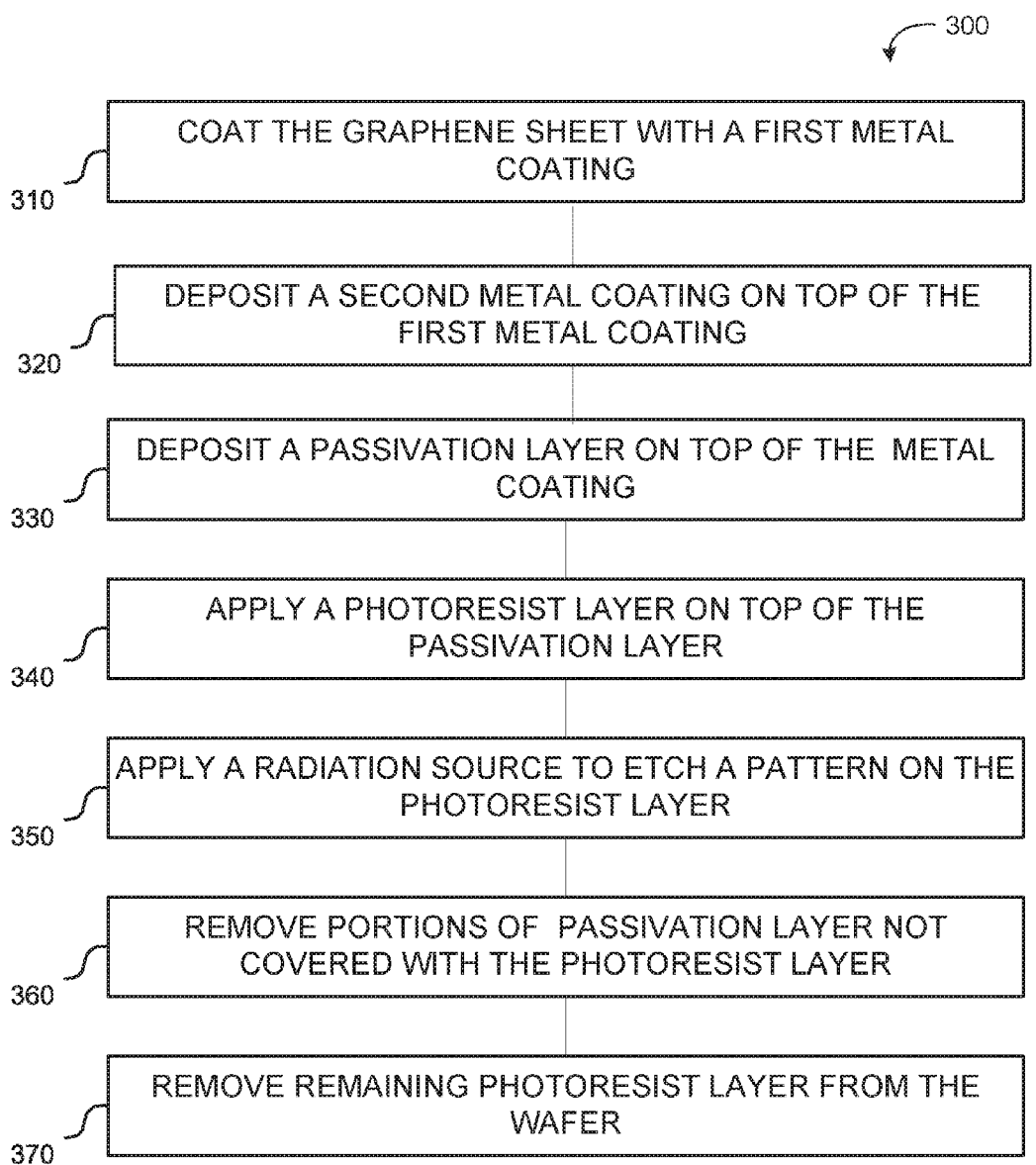
FIG. 3 is a flow chart illustrating a method for depositing a passivation layer onto a wafer according to one embodiment.

FIG. 3 is a flow chart illustrating a method 300 for depositing a passivation layer onto a wafer according to one embodiment. The exemplary method 300 includes depositing a gold metal coating at step 310 onto the graphene sheet. However, it should be noted that the graphene sheet is not limited to a gold metal coating, and instead, may also be coated with a wide range of other inert metals. Examples may include, but are not limited to, ruthenium, rhodium, palladium, silver, osmium, iridium, platinum and the like.

The gold metal coating may act as a protective barrier or mask configured to protect the graphene from being contaminated or damaged while preparing the graphene for use within the graphene based device. Due to gold's inert nature, the gold metal coating may protect the graphene from being damaged or degraded, especially when treating and exposing the graphene to high temperatures during epoxy curing, soldering, and burn testing by way of example only. Additionally, the gold metal coating may further prevent the graphene from being contaminated, especially when exposing and treating the graphene to solder vapor, harsh chemicals, wire bonding, dicing, and cleaning.

Next, exemplary method 300 may proceed to depositing a second metal coating on top of the first metal coating at step 320. The metal for the second metal coating may include any one of titanium, aluminum, chrome, nickel, and titanium nitride.

Next, exemplary method 300 may include depositing a passivation layer on top of the second metal coating at step 330. Because most metals used to create the metal contact leads are conductors, a passivation layer is deposited over the metal connections on the graphene wafer to help prevent electrical currents from leaking and damaging the graphene based devices. The passivation layer may be an dielectric layer, such as silicon dioxide. However, other materials such as silicon nitride, silicon oxide, amorphous silicon, and polysilicon may also be used.

Because depositing a passivation layer on the wafer completely covers all of the metal contact leads on the wafer, the passivation layer may be patterned such that the metal leads are exposed. In other words, this allows for graphene wells to be produced. However, before patterning the passivation layer directly, a photoresist layer may first be deposited over the passivation layer at step 340. A photoresist layer may be coated over the passivation layer because the photoresist layer may act as a temporary mask that acts as a patterning template when patterning the passivation layer via etching techniques.

For example, at step 350, select areas of the photoresist layer may be exposed to a radiation source, such that those exposed areas are etched away to create the desired pattern. Because portions of the photoresist layer are etched away, some portions of the passivation layer underneath the photoresist layer are now exposed to the environment. The exposed areas of the passivation layer may then be etched at step 360, such that the passivation layer is patterned according to the etched pattern template of the photoresist layer.

Once the passivation layer is patterned and etched accordingly, the metal contact leads are now properly exposed to the environment. As a result, the necessary chemical and biological sensing may occur via the exposed metal contact leads. The entire photoresist layer may then be removed from the passivation layer at step 370.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method for producing a graphene well comprising:
 placing a graphene sheet on a substrate;
 depositing a gold layer on top of the graphene sheet by dipping the graphene sheet in a gold plating solution;
 depositing a passivation layer on top of the gold layer; and
 depositing a photoresist layer on top of the passivation layer;
 wherein the depositing the passivation layer comprises a deposition process utilizing temperatures ranging from 100° C. to 200° C.

2. The method of claim 1, further comprising depositing a second metal layer between the gold layer and the passivation layer.

3. The method of claim 2, wherein the second metal layer comprises titanium, aluminum, chrome, nickel, or titanium nitride.

4. The method of claim 1, wherein the passivation layer comprises a dielectric layer.

5. The method of claim 4, wherein the dielectric layer comprises silicon dioxide, silicon nitride, silicon oxide, amorphous silicon, or polysilicon.

6. The method of claim 1, further comprising etching the photoresist layer to expose a surface of the passivation layer.

7. The method of claim 6, wherein the etching of the photoresist layer comprises applying an acetone rinse and applying an isopropanol alcohol rinse.

8. The method of claim 1, further comprising removing the passivation layer by a dry etching technique.

9. The method of claim 1, wherein depositing the passivation layer comprises applying a plasma enhanced chemical vapor deposition process.

10. A method for producing a graphene well comprising:
 placing a graphene sheet on a substrate;
 depositing a first metal layer comprising gold on top of the graphene sheet by dipping the graphene sheet in a gold plating solution;
 depositing a passivation layer on top of the first metal layer;
 depositing a photoresist layer on top of the passivation layer; and
 etching a pattern on the photoresist layer to expose a surface of the passivation layer;
 wherein the depositing the passivation layer comprises a deposition process utilizing temperatures ranging from 100° C. to 200° C.

11. The method of claim 10, further comprising depositing a second metal layer between the first metal layer and the passivation layer.

12. The method of claim 11, wherein the second metal layer comprises titanium, aluminum, chrome, nickel, or titanium nitride.

13. The method of claim 1, wherein the passivation layer comprises a dielectric layer.

* * * * *